(12) United States Patent
Stark

(10) Patent No.: US 9,775,683 B2
(45) Date of Patent: *Oct. 3, 2017

(54) MEDICAL WASTE CONTAINERS AND LIDS THEREFORE

(71) Applicant: Becton, Dickinson and Company, Franklin Lakes, NJ (US)

(72) Inventor: Kenneth O. Stark, San Marcos, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/386,551

(22) Filed: Dec. 21, 2016

(65) Prior Publication Data

US 2017/0100200 A1    Apr. 13, 2017

Related U.S. Application Data

(60) Continuation of application No. 15/072,813, filed on Mar. 17, 2016, now Pat. No. 9,561,084, which is a (Continued)

(51) Int. Cl.
*B65D 83/10* (2006.01)
*B65D 51/18* (2006.01)
(Continued)

(52) U.S. Cl.
CPC ............ *A61B 50/362* (2016.02); *B65D 55/16* (2013.01); *B65F 1/02* (2013.01); *B65F 1/1607* (2013.01);
(Continued)

(58) Field of Classification Search
CPC .......... A61B 50/362; A61B 2050/0059; A61B 2050/0082; A61B 2050/0089
(Continued)

(56) References Cited

U.S. PATENT DOCUMENTS 501,636 A    7/1893 Welds
505,082 A    9/1893 Von Ainbach
(Continued)

FOREIGN PATENT DOCUMENTS

CA    2357277    3/2003
DE    9102648    6/1991
(Continued)

OTHER PUBLICATIONS

"PCT International Preliminary Report on Patentability and Written Opinion in PCT/US2012/054788", mailed Apr. 10, 2014, 10 pages.

*Primary Examiner* — Luan K Bui
(74) *Attorney, Agent, or Firm* — Servilla Whitney LLC

(57) ABSTRACT

Waste container lid assemblies configured for attachment to a base having a lid body and cap portion slidably connected by a tether. The lid body having an opening sized to accept medical waste and restrict access to prevent individuals from reaching into the waste container through the opening. A slot is in the lid body to permit slidable movement of the tether through the slot such the cap can be moved from a resting position in which the opening is configured for receiving waste to a closed position such that the cap portion covers the opening.

10 Claims, 4 Drawing Sheets

Related U.S. Application Data division of application No. 13/250,501, filed on Sep. 30, 2011, now Pat. No. 9,320,567.

(51) Int. Cl.
*A61B 50/36* (2016.01)
*B65D 55/16* (2006.01)
*B65F 1/02* (2006.01)
*B65F 1/16* (2006.01)
*A61B 50/00* (2016.01)

(52) U.S. Cl.
CPC .... *B65F 1/1615* (2013.01); *A61B 2050/0059* (2016.02); *A61B 2050/0082* (2016.02); *A61B 2050/0084* (2016.02); *A61B 2050/0089* (2016.02); *B65F 2001/1676* (2013.01)

(58) Field of Classification Search
USPC ........ 206/363–370; 220/254.3, 254.9, 259.5, 220/375
See application file for complete search history.

(56) References Cited

U.S. PATENT DOCUMENTS

| | | | |
|---|---|---|---|
| 4,047,648 A * | 9/1977 | Croyle | B65D 47/0895 220/375 |
| 4,082,201 A * | 4/1978 | Bittel | B65D 47/147 215/306 |
| 4,328,907 A | 5/1982 | Beard | |
| 4,452,358 A | 6/1984 | Simpson | |
| 4,454,944 A | 6/1984 | Shillington | |
| 4,462,507 A | 7/1984 | Margulies | |
| 4,502,606 A * | 3/1985 | Shillington | A61M 5/3205 215/274 |
| D279,417 S | 6/1985 | Spencer | |
| 4,520,926 A | 6/1985 | Nelson | |
| D292,777 S | 11/1987 | Shillington | |
| 4,714,353 A * | 12/1987 | Leaphart | D06F 95/006 220/375 |
| 4,779,766 A | 10/1988 | Kinsley | |
| D302,291 S | 7/1989 | Heubel | |
| 4,874,103 A * | 10/1989 | Quisenberry | B65F 1/1607 206/366 |
| 4,930,655 A | 6/1990 | Wells | |
| 4,974,744 A * | 12/1990 | Shanklin | A47G 23/0258 220/254.1 |
| D330,765 S | 11/1992 | Laws | |
| 5,165,563 A | 11/1992 | McKendry | |
| 5,405,034 A | 4/1995 | Mittel, Jr. | |
| D371,963 S | 7/1996 | Ahern, Jr. | |
| 5,941,385 A | 8/1999 | Barton | |
| 6,062,001 A * | 5/2000 | Kunik | A61M 5/3205 206/366 |
| 6,131,755 A | 10/2000 | Soyka, Jr. | |
| 6,158,632 A | 12/2000 | Ekkert | |
| 6,364,101 B1 | 4/2002 | Schultz | |
| D461,447 S | 8/2002 | Nawrozki | |
| 6,585,114 B2 * | 7/2003 | Kennedy | A61M 5/3205 206/366 |
| D482,448 S | 11/2003 | Crawford | |
| D485,906 S | 1/2004 | Danssaert | |
| 6,986,434 B1 | 1/2006 | Getsy | |
| 6,997,313 B2 | 2/2006 | Rigling | |
| 7,445,116 B2 | 11/2008 | Dansaert | |
| D591,859 S | 5/2009 | Stark | |
| D606,885 S | 12/2009 | Olsson | |
| D623,817 S | 9/2010 | Yang | |
| D630,940 S | 1/2011 | Shapiro | |
| D642,048 S | 7/2011 | Ocampo | |
| D661,182 S | 6/2012 | Noer | |
| D671,830 S | 12/2012 | Hudson | |
| D674,571 S | 1/2013 | Sakaguchi | |
| D682,689 S | 5/2013 | Kalberer | |
| 2004/0112896 A1 | 6/2004 | Lewis | |
| 2004/0217117 A1 | 11/2004 | Lien | |
| 2006/0249471 A1 | 11/2006 | Leposavic | |
| 2008/0105696 A1 * | 5/2008 | Dart | B65D 43/0212 220/711 |
| 2010/0032441 A1 | 2/2010 | Stark | |
| 2013/0081965 A1 | 4/2013 | Stark | |

FOREIGN PATENT DOCUMENTS

| | | |
|---|---|---|
| EP | 0569233 | 11/1993 |
| EP | 2760364 | 8/2014 |
| JP | H03500850 A | 2/1991 |
| JP | 2005525270 A | 8/2005 |

\* cited by examiner

MEDICAL WASTE CONTAINERS AND LIDS THEREFORE

CROSS-REFERENCE TO RELATED APPLICATIONS

This application is a continuation of U.S. patent application Ser. No. 15/072,813 filed Mar. 17, 2016, now U.S. Pat. No. 9,561,084, which is a divisional of U.S. patent application Ser. No. 13/250,501, filed Sep. 30, 2011, now U.S. Pat. No. 9,320,567, the entire disclosures of which are hereby incorporated by reference herein.

BACKGROUND

The present invention relates to medical waste disposal containers and lids for such containers, particularly containers for used sharp medical devices, which may require temporary and permanent closure.

The safe and efficient disposal of sharp medical devices such as surgical knives, blades, hypodermic needles and the like is a problem for medical and other healthcare facilities. Disposable containers have been developed in recent years which provide a reasonably high degree of security for disposable sharps articles and materials from hospitals and clinics. Many of these articles, such as needles and surgical blades known as sharps, and other similar articles and materials, must be disposed of in a manner to keep them out of the hands of unauthorized persons and to keep them from being reused.

The containers are normally designed to prevent the removal of materials from the container under ordinary circumstances until permanently closed. Commonly used Horizontal Entry Opening containers, which accommodate a counter-balance door restrict human access to the contents of the container by creating a torturous path when a person attempts to put their hand into the container. Unfortunately, this same restricted access can prohibit the disposal of certain objects through the opening. Any object disposed of must impact the counter-balanced door and the weight of the disposed item will rotate the door moving it out of the opening and allowing the item to drop into the container. This creates an opportunity for very light, unusually shaped or sticky items to become hung up on the door warranting additional manipulation from the user to finish the disposal of the item increasing the risk of danger to the user from contamination or needle sticks.

Accordingly, there is an ongoing need in the art for containers which restricts human access to the contents and provides an opening of sufficient size to allow disposal of large or oddly shaped items.

SUMMARY OF THE INVENTION

One or more embodiments are directed to waste containers comprising a base and a lid assembly. The base has a bottom wall, a side wall extending upwardly from the bottom wall and defining a receptacle for receiving medical waste. The lid assembly includes a lid body configured for assembly to the base and a cap portion. The cap portion is connected to the lid body and covers an opening in the lid body. The opening being sized to accept medical waste and restrict access to prevent individuals from reaching into the waste container through the opening. A tether slidably connects the cap portion to the lid body. A slot is in the lid body to permit slidable movement of the tether through the slot such the cap can be moved from a resting position such that the opening is configured for receiving waste to a closed position such that the cap portion covers the opening. In some embodiments, the cap portion and tether are integrally formed. In specific embodiments, the lid assembly is made of a thermoplastic material.

In some embodiments, the opening is located in a forward portion of the lid body and the slot is located in a rearward portion of the lid body. The tether engages the slot such that the cap portion is permitted to move forwardly and rearwardly. In detailed embodiments, the lid body includes a raised surface extending from an upper surface of the lid body that engages the cap portion when the cap portion is in the resting position. In specific embodiments, the cap portion includes a recess configured to engage the raised surface. In detailed embodiments, the forward portion and the rearward portion are tilted relative to each other.

In some embodiments, the slot is located adjacent the raised surface. In detailed embodiments, the slot is located within the raised surface. In specific embodiments, the raised surface defines a notched area, and the slot is located within the notched area.

In one or more embodiments, the opening is surrounded by a raised peripheral lip extending from an upper surface of the lid body, and the cap portion includes a peripheral channel to engage the raised peripheral lip. In detailed embodiments, the cap portion includes at least a pair of locking tabs and lid body includes at least a pair of slits positioned to accept the locking tabs to lock the cap portion in a closed position. In specific embodiments, the locking tabs include radially projecting fins sized to provide an interference fit when sliding through the slits into the closed position and prevent removal of the cap portion from the lid body.

Additional embodiments of the invention are directed to waste container lid assemblies including a lid body configured for assembly to a container base. The waste container lid assembly comprises a cap portion connecting to the lid body that covers an opening in the lid body, the opening located in a forward portion of the lid body and sized to accept medical waste and restrict access to prevent individuals from reaching into the waste container through the opening. A tether engages the slot and slidably connecting the cap portion to the lid body, permitting the cap portion to move forwardly and rearwardly. A slot located in a rearward portion of the lid body to permit slidable movement of the tether through the slot such the cap can be moved from a resting position such that the opening is configured for receiving waste to a closed position such that the cap portion covers the opening.

In some embodiments, the lid body includes a raised surface extending from an upper surface of the lid body that engages the cap portion when the cap portion is in the resting position. In detailed embodiments, the cap portion includes a recess configured to engage the raised surface. In specific embodiments, the raised surface defines a notched area, and the slot is located within the notched area.

In some embodiments, the opening is surrounded by a raised peripheral lip extending from an upper surface of the lid body, and the cap portion includes a peripheral channel to engage the raised peripheral lip. In detailed embodiments, the cap portion includes at least a pair of locking tabs and lid body includes at least a pair of slits positioned to accept the locking tabs to lock the cap portion in a closed position. In specific embodiments, the locking tabs include radially projecting fins sized to provide an interference fit when sliding through the slits into the closed position and prevent removal of the cap portion from the lid body.

The various embodiments and aspects of the invention described here can be employed individually or in conjunction.

DETAILED DESCRIPTION

Figure 1:
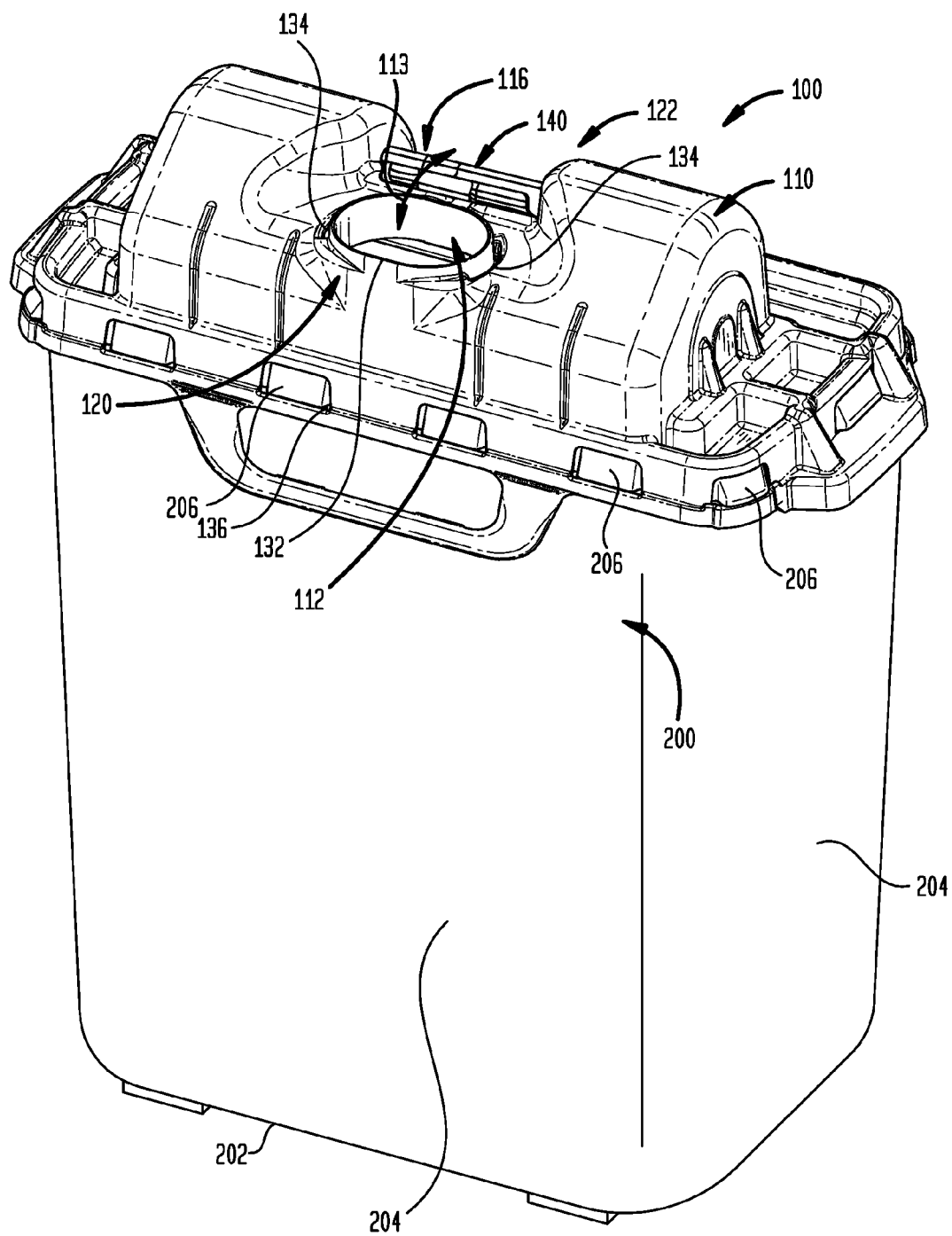
FIG. 1 is a top front perspective view of a medical waste container with a lid assembly according to one or more embodiments in which the cap portion is in the open resting position.

Before describing several exemplary embodiments of the invention, it is to be understood that the invention is not limited to the details of construction or process steps set forth in the following description. The invention is capable of other embodiments and of being practiced or being carried out in various ways.

Embodiments of the invention are directed to medical waste container tops and closures with a redesigned access opening which fits existing sharps collector bases for a patient room sharps collector. The closure of various embodiments is retained to the top via a tether near, but not over, the opening allowing unobstructed access to the opening during use. The top, with closure, may be snapped onto a base which is then placed into a patient room wall mounted cabinet or bracket. The opening is accessible for one handed disposal of sharps and medical waste during normal use. After the collector is full, the closure is snapped and locked over the opening for disposal.

Embodiments of the invention are intended for vertical disposal of sharps waste as opposed to horizontal disposal. For example, a syringe can be disposed of by dropping the syringe (e.g., point first) into the collector as opposed to a horizontal orientation as in alternate designs. The smaller open vertical entry design restricts human access to the contents by having a reduced opening size large enough for disposal of sharps and medical waste, but small enough to prohibit the insertion of hands.

The straight through design of the vertical entry opening allows for the free fall disposal of items when disposed of into the container. Items such as blood collection units with tubing attached can be fed into the opening and dropped without the need for additional manipulation from the user. By eliminating the horizontal entry counter-balanced door and utilizing the straight through vertical entry, there is nothing present which may impede disposal of certain items. Many users have higher disposal rates of unusually shaped devices and need to be able to dispose of the items in a consistent and safe manner.

The present invention pertains to a waste container lid and waste containers including such lids. FIGS. 1-5 show an exemplary embodiment a waste container lid assembly 100. The lid assembly 100 is configured for assembly to a base 200. The base 200 includes a bottom wall 202, at least one side wall 204 extending upwardly from the bottom wall 202. The at least one side wall 204 and the bottom wall 202 forming and defining a receptacle suitable for receiving medical waste. The bottom wall 202 and at least one side wall 204 of the base 200 can be integrally formed so that the base appears to be an integrally formed single unit. Any suitable base 200 can be employed and it should be understood that the invention is not limited to any particular style or material.

The lid assembly 100 is composed of two main parts, a lid body 110 and a cap portion 140. The cap portion 140 is connected to the lid body 110 and, in one position, covers an opening 112 in the lid body 110. The opening 112 is sized to accept medical waste and restrict access to prevent individuals from reaching into the waste container through the opening 112. The opening 112 can be any suitable size or shape. For example, the opening 112 shown in the Figures is oval shaped. In various embodiments, the opening 112 is round, oval, square, rectangular, oblong, trapezoidal, rhomboid, rectangular with rounded corners. It should be understood that these shapes are merely illustrative of possible openings and that other shapes may be employed.

Figure 3:
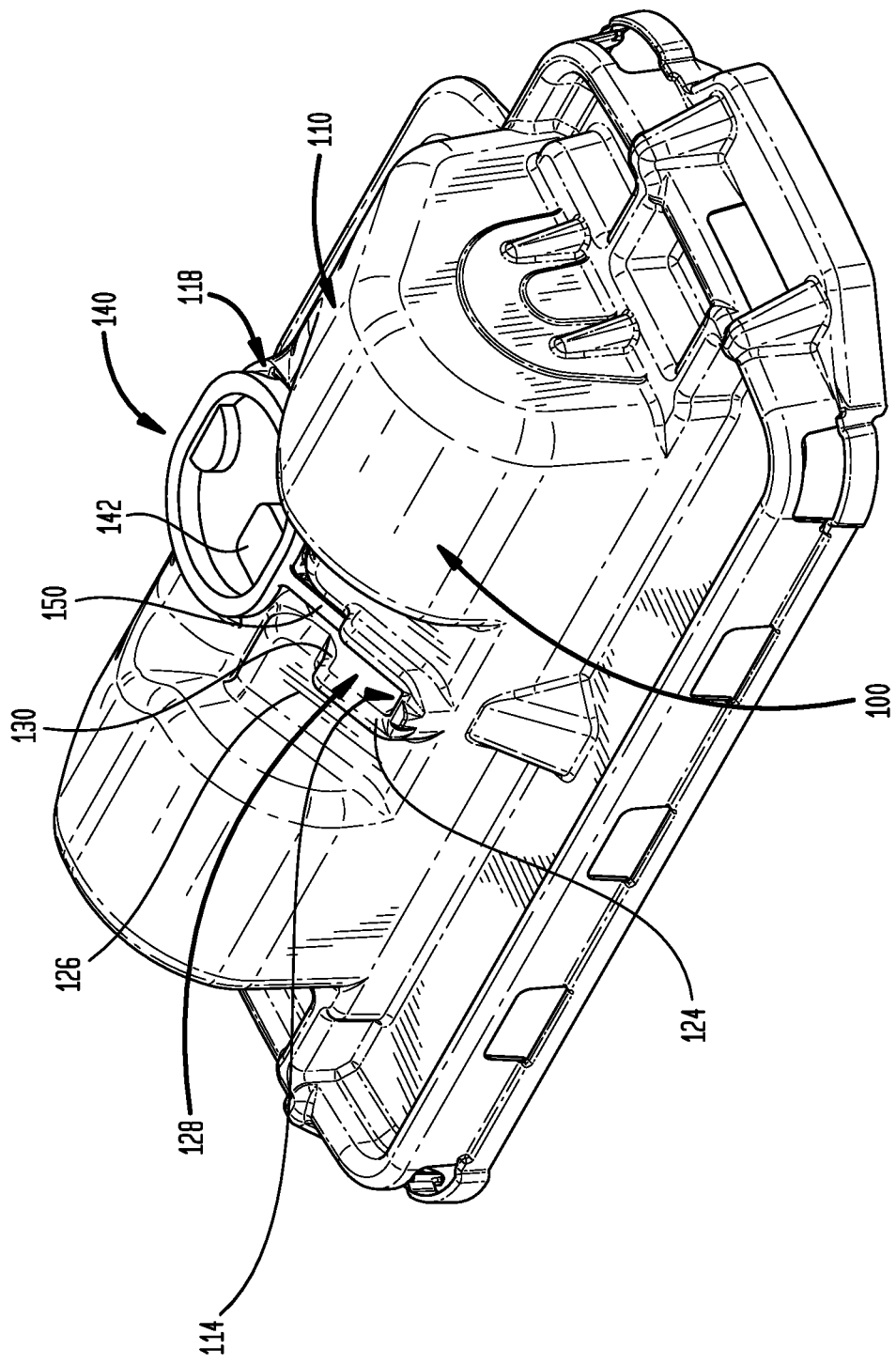
FIG. 3 is a top front perspective view of a waste container lid assembly with the cap portion in the closed position.
Figure 4:
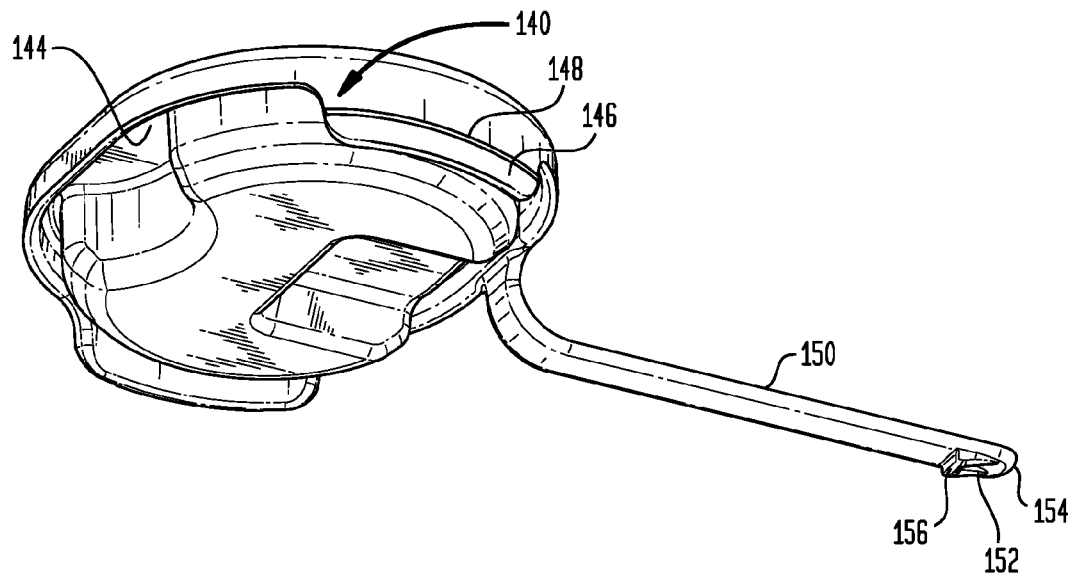
FIG. 4 is a bottom front perspective view of a cap portion of a lid assembly in accordance with one or more embodiments of the invention.
Figure 5:
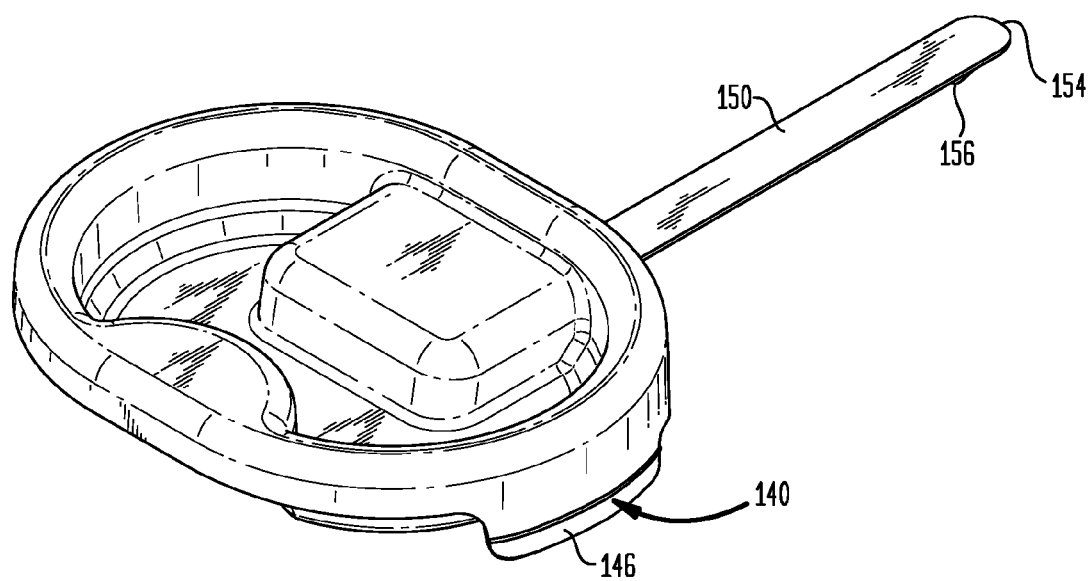
FIG. 5 is a top rear perspective view of a cap portion of a lid assembly in accordance with one or more embodiments of the invention.

The lid body 110 and the cap portion 140 are connected by a tether 150. The tether 150 can be integrally formed with the cap portion 140, as shown in FIGS. 4 and 5, or can be separate components with a suitable connection. The tether 150 slidably connects the cap portion 150 to the lid body 110 via a slot 114 in the lid body 110. The tether is sized to allow the cap to slide between the open or resting position in FIG. 1 and the closed position in FIG. 3. The slot permits slidable movement of the tether 150 through the slot such that the cap portion 140 can be moved from a resting position 116 to a closed position 118. As shown in FIGS. 4 and 5, the tether 150 may include a barb 152 suitable for preventing the cap portion 140 from becoming disconnected from the lid body 110. The barb 152 of some embodiments has a tapered shape with a narrow end 154 flaring to a wide portion 156. The wide portion 156 being sized slightly larger than the slot 114. This enables the tether to be inserted through the slot 114 from the narrow end 154 and prevents the tether 150 from being completely removed from the slot 114 by interaction of the wide portion 156 with the slot 114. This barb 152 may also be referred to as a bayonet style locking tab.

In the resting position 116 (see FIG. 1), the cap portion 140 is positioned such that the opening 112 is configured for received waste. In some embodiments, when the cap portion 140 is positioned in the resting position 116, the opening 112 is unobstructed by the cap portion 140. In the closed position 118, the cap portion 140 covers the opening 112. In detailed embodiments, in the closed position 118, the cap portion 140 covers the opening 112 and substantially completely obstructs the opening and permanently closes the lid assembly, preventing access to the contents of the base 200. As used in this specification and the appended claims, "permanently closing" refers to a condition in which the contents of the container cannot be accessed through the opening without using either a tool specifically designed to remove the cap portion 140 from the opening 112 or requiring the substantial destruction of at least a portion of the lid assembly. In other words, permanently closing is intended to lock the container to prevent unauthorized access of the container after it has been locked by a medical practitioner and the container is ready for disposal.

In some embodiments, the opening 112 is located in a forward portion 120 of the lid body 110 and the slot 114 is located in a rearward portion 122 of the lid body 110. Stated differently, the opening 112 is a hole through the major plane of the forward portion 120 and the slot is an elongate hole in the major plane of the rearward portion 122 of the lid body 110. The tether 150 engages the slot 114 such that the cap portion 140 is permitted to move forwardly and rearwardly along path 113. In detailed embodiments, moving the cap portion 140 from the resting position 116 to the closed position 118 requires substantially only forward movement. As used in this specification and the appended claims, the term "substantially only forward movement" means that little or no side to side movement of the cap portion 140 is required to move from the resting position 116 to the closed position 118, or to move from the rearward portion 122 to the forward portion 120.

The forward portion 120 and the rearward portion 122 can be substantially coplanar, meaning that the front and back are approximately flat, or tilted relative to each other. FIG. 1, shows an embodiment where the forward portion 120 is substantially flat so that it is substantially horizontal with the rearward portion angled back, away from the forward portion 120. This configuration may be useful in both presenting the opening in an upright state to the user and in helping keep the cap portion 140 from being accidentally pulled over the opening 112. In other embodiments, the forward portion 120 is tilted forward, toward the user, and the rearward portion 122 is either approximately level or tilted slightly backward.

In some embodiments, the lid body 110 includes a raised surface 124 extending from an upper surface 126 of the lid body 110. Stated differently, the raised surface 124 is a portion that extends above the major plane of the lid body 110. In some embodiments, the raised surface 124 extends above the major plane of the rearward portion 122 of the lid body 110. The raised surface 124 can engage the cap portion 140 when the cap portion 140 is in the resting position 116. In detailed embodiments, as shown in FIG. 3, the cap portion 140 includes a recess 142 configured to engage the raised surface 124. This engagement can be of a cooperative nature such that there is little or no force required to disengage the cap portion 140 from the raised surface 124, or can have a friction fit so that the cap portion 140 does not become inadvertently dislodged from the raised surface 124.

Figure 2:
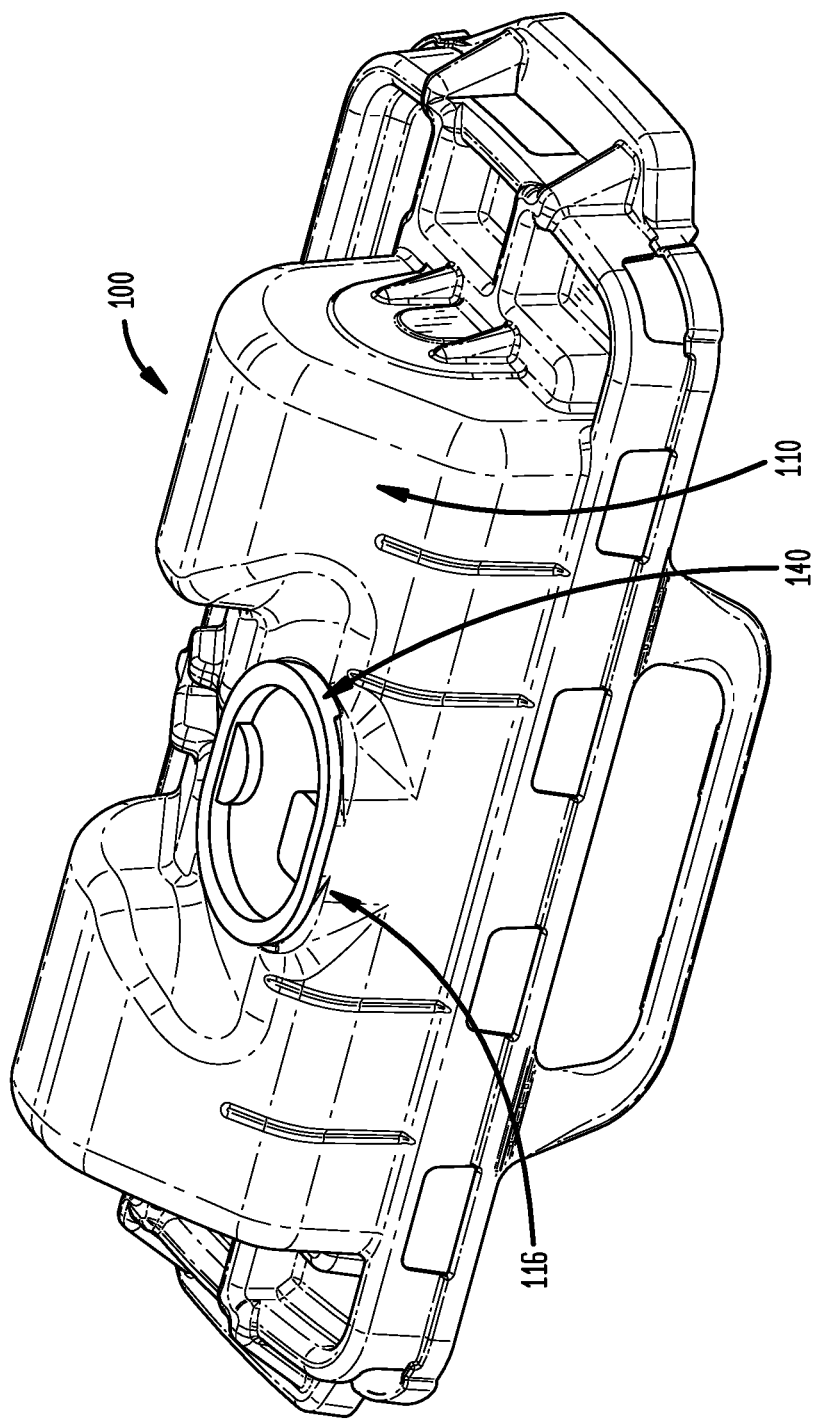
FIG. 2 is a top rear perspective view of a medical waste container lid assembly according to one or more embodiments with the cap portion in the open resting position.

In the detailed embodiments shown in FIGS. 2 and 3, the cap portion 140 rests on the raised surface 124 which has a rectangular horseshoe configuration including a channel 130. With the raised surface 124 located in the rearward portion 122 of the lid body 110, the cap portion 140, when in the resting position 116 is located adjacent the rearward portion 122. The rectangular horseshoe configuration defines the notched area 128 and the channel guides the movement of the tether 150. In detailed embodiment, the notched area 128 is in the major plane of the rearward portion 122 of the lid body 110. When in the resting position 116, the cap portion 140 can rest over the raised surface 124 so that the waste can be disposed within the container through the opening 112. The cap portion 140 may include a rectangular recess 142 configured to cooperatively interact with the rectangular horseshoe configuration of the raised surface 124. Additionally, the cap portion 140 can have a recess 142 of any suitable shape for forming a cooperative interaction with the raised surface 124, depending on the shape of the raised surface 124.

The slot 114 can be located adjacent the raised surface 126 or within the raised surface 124. For example, the slot can be at the base of the raised surface so that the slot is on the upper surface 126 of the lid body 110. In detailed embodiments, the slot is located on a side wall of the raised surface 124 and not on the upper surface of the lid body 110. In specific embodiments, as seen in the Figures, the raised surface 124 defines a notched area 128 and the slot 114 is located within the notched area 128.

Referring to FIG. 1, the opening 112 may be surrounded by a raised peripheral lip 132 extending from the upper surface 126 of the lid body 110. The raised peripheral lip 132 extends above the major plane of the frontward portion 120. The cap portion 140 in these embodiments, as shown in FIG. 4, includes a peripheral channel 144 configured to engage the raised peripheral lip 132 surrounding the opening 112. As seen in FIG. 1, the raised peripheral lip 132 projects or protrudes upwardly from the upper surface 126 of the lid body 110, and when the cap is placed in the closed position 118 (as shown in FIG. 3), the cap portion 140 also projects beyond the upper surface 126 of the lid body 110.

As shown in FIGS. 4 and 5, the cap portion 140 of one or more embodiments includes at least a pair of locking tabs 146 and lid body 110 includes at least a pair of slits 134 positioned adjacent the opening 112 to accept the locking tabs 146 to lock the cap portion 140 in the closed position 118. The locking tabs 146 of specific embodiments have a bayonet style locking interaction. The slits 134 in the lid body 110 can be positioned outside and adjacent the raised peripheral lip 132. In detailed embodiment, the locking tabs 146 include radially projecting fins 148 sized to provide an interference fit when sliding through the slits 134 into the closed position. When the container is filled or no longer needed, the cap portion 140 is pulled from the resting position 116 over the opening 112 using a sliding motion and snapped in place with bayonet tabs (locking tabs 146) fitting into the slits 134 adjacent the opening 112.

The base (waste container) and the lid assembly of one or more embodiments are molded from thermoplastic materials. In detailed embodiments, the lid assembly 110 and base 200 are separate parts which can be permanently attached. As used in this specification and the appended claims, the term "permanently attached" means that the lid assembly cannot be easily removed from the base without specific tools designed for the purpose or without causing damage to either the base or lid assembly. Suitable structures for permanently attaching the lid assembly 110 to the base 200 include, but are not limited to, protrusions 206 on an upper portion of the base 200 which fit into matching openings 136 in the lid assembly 110.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A waste container comprising:
   a base having a bottom wall, a side wall extending upwardly from the bottom wall and defining a receptacle for receiving medical waste; and
   a lid assembly including a lid body configured for assembly to the base,
      a cap portion connected to the lid body that covers an opening in the lid body, the cap portion including at least a pair of locking tabs and the lid body including at least a pair of slits positioned to accept the locking tabs to lock the cap portion in a closed position, wherein the locking tabs include radially projecting fins sized to provide an interference fit when sliding through the slits into the closed position and prevent removal of the cap portion from the lid body; the opening being sized to accept medical waste and restrict access to prevent individuals from reaching into the waste container through the opening, and the opening being surrounded by a raised peripheral lip extending from an upper surface of the lid body, and the cap portion includes a peripheral channel to engage the raised peripheral lip,
      a tether slidably connecting the cap portion to the lid body, and
      a slot in the lid body to permit slidable movement of the tether through the slot such the cap can be moved from a resting position such that the opening is configured for receiving waste to a closed position such that the cap portion covers the opening.

2. The waste container lid assembly of claim 1, wherein the opening is located in a forward portion of the lid body and the slot is located in a rearward portion of the lid body, the tether engages the slot such that the cap portion is permitted to move forwardly and rearwardly.

3. The waste container of claim 2, wherein the lid body includes a raised surface extending from an upper surface of the lid body that engages the cap portion when the cap portion is in the resting position.

4. The waste container of claim 3, wherein the cap portion includes a recess configured to engage the raised surface.

5. The waste container lid assembly of claim 3, wherein the slot is located adjacent the raised surface.

6. The waste container lid assembly of claim 3, wherein the slot is located within the raised surface.

7. The waste container of claim 6, wherein the raised surface defines a notched area, and the slot is located within the notched area.

8. The waste container lid assembly of claim 1, wherein the cap portion and tether are integrally formed.

9. The waste container lid assembly of claim 2, wherein the forward portion and the rearward portion are tilted relative to each other.

10. The waste container lid assembly of claim 1, wherein the lid assembly is made of a thermoplastic material.

* * * * *